United States Patent
Erdmann et al.

(10) Patent No.: US 10,561,159 B2
(45) Date of Patent: *Feb. 18, 2020

(54) PROCESS FOR TREATING A SWEET WHEY MATERIAL CONTAINING CGMP AND RELATED METHOD FOR PRODUCING A PROTEIN MATERIAL HAVING A TARGETED TRYPTOPHAN/THREONINE RATIO

(71) Applicant: NESTEC S.A., Vevey (CH)

(72) Inventors: Peter Erdmann, Bern (CH); Gustavo Rocha, Freimettigen (CH); Gerard Terpstra, Cordast (CH)

(73) Assignee: Societe des Produits Nestle S.A., Vevey (CH)

( * ) Notice: Subject to any disclaimer, the term of this patent is extended or adjusted under 35 U.S.C. 154(b) by 75 days.

This patent is subject to a terminal disclaimer.

(21) Appl. No.: 15/547,621

(22) PCT Filed: Feb. 2, 2016

(86) PCT No.: PCT/EP2016/052174
§ 371 (c)(1),
(2) Date: Jul. 31, 2017

(87) PCT Pub. No.: WO2016/128254
PCT Pub. Date: Aug. 18, 2016

(65) Prior Publication Data
US 2018/0263258 A1   Sep. 20, 2018

(30) Foreign Application Priority Data
Feb. 9, 2015 (EP) .................................. 15154372

(51) Int. Cl.
*A23J 1/20* (2006.01)
*C07K 1/18* (2006.01)

(52) U.S. Cl.
CPC ................. *A23J 1/205* (2013.01); *C07K 1/18* (2013.01)

(58) Field of Classification Search
CPC .......... A23J 1/205; A23L 331/19; A23L 33/40
(Continued)

(56) References Cited

U.S. PATENT DOCUMENTS 6,787,158 B1 * 9/2004 Erdmann et al.
2014/0377439 A1 * 12/2014 Erickson
2015/0272191 A1 * 10/2015 Van Goudoever et al.

FOREIGN PATENT DOCUMENTS

EP     0488589 A1    6/1992
EP     1048226       11/2000
(Continued)

OTHER PUBLICATIONS

Russia Patent Office Communication for Application No. 2017131484/10(055130) dated Aug. 27, 2019, 6 pages.

*Primary Examiner* — Helen F Heggestad
(74) *Attorney, Agent, or Firm* — K&L Gates LLP (57) ABSTRACT

Process for the treatment of a sweet whey material (SWM) containing cGMP (caseinoGlycoMacroPeptide), comprising the following steps: Decationising the SWM material so as to obtain a sweet whey SW having a pH value of 1 to 4.5; Treating said SW in a fluidized bed reactor comprising a volume of an anionic resin, at 10 to 18° C., wherein said SW contacts said resin so that the resin absorbs between 0% and 100% of the cGMP present in the SW; and Recovering a protein material; Wherein the treating is such that the resin absorbs 30 to 45 g/L of the cGMP present in the sweet whey. Method for producing a protein material from a SWM cGMP, said protein material having a targeted tryptophan/threonine (Trp/Thr) ratio, comprising the following steps: —Implementing the treating process twice, wherein the resins absorbs P1 of the cGMP, obtaining a first protein
(Continued)

material having Trp/Thr1 and wherein the resins absorbs a percentage P2 of the cGMP, obtaining a second protein material having Trp/Thr2; —Drafting the linear calibration curve in a graph (cGMP %; Trp/Thr) by positioning (Trp/Thr1; P1) and (Trp/Thr2; P2) and drawing a line through these two plots; —Determining the specific ratio of cGMP present in the SW that the resin should absorb with respect to the targeted Trp/Thr by the calibration curve; and —Implementing the process of the invention on the SWM wherein the resins absorbs the specific ratio of cGMP, so that to obtain the protein material having the targeted Tp/Thr.

2 Claims, 3 Drawing Sheets

(58) Field of Classification Search
 USPC .................................. 426/656, 583, 478, 491
 See application file for complete search history.

(56) References Cited

FOREIGN PATENT DOCUMENTS

| | | |
|---|---|---|
| RU | 2260284 C2 | 9/2005 |
| WO | 0141580 | 6/2001 |

\* cited by examiner

PROCESS FOR TREATING A SWEET WHEY MATERIAL CONTAINING CGMP AND RELATED METHOD FOR PRODUCING A PROTEIN MATERIAL HAVING A TARGETED TRYPTOPHAN/THREONINE RATIO

CROSS REFERENCE TO RELATED APPLICATIONS

The present application is a National Stage of International Application No. PCT/EP2016/052174, filed on Feb. 2, 2016, which claims priority to European Patent Application No. 15154372.5, filed on Feb. 9, 2015, the entire contents of which are being incorporated herein by reference.

TECHNICAL FIELD

The invention is directed to a process for the treatment of a sweet whey material containing cGMP (caseinoGlycoMacroPeptide), and a related method for producing a protein material from a sweet whey material containing cGMP (caseinoGlycoMacroPeptide), said protein material having a targeted tryptophan/threonine ratio.

BACKGROUND OF THE INVENTION

U.S. Pat. No. 687,158 relates to a process for the extraction of glycomacropeptide or caseinoglycomacropeptide ("cGMP") from a lactic raw material. cGMP is a phosphorylated and partially sialylated macropeptide which is formed by the action of a protease, for example rennet, on mammalian milk kappa-casein. cGMP represents about 20% by weight of the proteins in sweet whey obtained after separation of casein during cheese manufacture.

This process comprises the steps of removing cations from a lactic raw material for a sufficient amount of time to obtain a substantially deionised lactic raw material having a pH of about 1 to 4.5; contacting the substantially deionised lactic raw material with an anionic resin having a hydrophobic matrix for a sufficient amount of time and at a sufficient temperature to remove cGMP from the substantially deionised lactic raw material and to obtain a treated liquid material; separating the resin from the treated liquid material; and rinsing the resin to obtain the cGMP therefrom. The cGMP is actually removed in a range from 85 to 91% of the starting cGMP.

The treated liquid material that is obtained from sweet whey has an amino acid profile reduced in threonine and enriched in aromatic amino acids such as tryptophan. It is useful in an infant or dietetic product as a protein source or raw material, in a pharmaceutical composition in combination with antithrombotic, antidiarrheal or antibacterial agents, or in a food composition as an emulsifying, gelling of foaming agent.

However, its amino acid profile, in particular the tryptophan and threonine contents, makes the treated liquid not always suitable for hypoallergenic formulae, and the manufacturer has to mix it with at least one different source of proteins and/or to add selected amino acids.

Moreover, the duration of the treatment and the amount of resin and treated liquid are chosen as a function of the composition of the starting material and the quantity of cGMP to be removed. In practice, this is achieved through experiments in the field work but no clear theoretical rule has emerged so as to facilitate the processing of the treatment.

Therefore one object of the invention is to provide a process for treating a sweet whey material comprising cGMP, on the basis of a simple and efficient setting, or to at least provide a useful alternative.

Another related object of the invention is to provide a method producing a protein material from a sweet whey material containing cGMP, said protein material having targeted tryptophan and threonine contents by the use of said process, or to at least provide a useful alternative.

SUMMARY OF THE INVENTION

In a first aspect of the invention there is provided a process for the treatment of a sweet whey material containing cGMP (caseinoGlycoMacroPeptide), said process comprising the following steps:
Decationising the sweet whey material so as to obtain sweet whey having a pH value of 1 to 4.5;
Treating said sweet whey in a fluidized bed reactor comprising a specific volume of an anionic resin, at a temperature between 10 and 18° C., wherein said sweet whey contacts said resin so that the resin absorbs between 0% and 100% of the cGMP present in the sweet whey; and
Recovering a protein material;
Wherein the treating is carried out for a sufficient time so that the resin absorbs 30 to 42 g/L, preferably between 35 and 42 g/L, more preferably between 39 and 41 g/L, of the cGMP present in the sweet whey.

The inventors have found that, surprisingly, the process has a key parameter, which has substantially a constant value whatever process is implemented, corresponding to a maximum of cGMP absorption in the resin. This maximum is reached after a sufficient time. This allows the process of the present invention to be implemented in an easy and efficient way.

The process is advantageously such that the protein material is suitable for hypoallergenic infant formulae. There is no need, as what was done before, to remove the cGMP at a high level (85 to 91 wt %), so that to have a treated material substantially with no cGMP, said treated liquid being mixed with at least one different source of proteins and/or amino acids in order to be suitable for infant formulae. In other words, cGMP can still partially be present in the protein material.

Furthermore, and surprisingly, whatever the level of absorption of cGMP by the resin is, undesired products such as anions (typically present in whey) are absorbed by the resin during the treatment process according to the invention so that they are present at acceptable levels (impurity traces) in the protein material, whatever the percentage of the cGMP absorption in the resin is.

In a second aspect of the invention there is provided a method for producing a protein material from a sweet whey material containing cGMP (caseinoGlycoMacroPeptide), said protein material having a targeted tryptophan/threonine ratio, wherein said method comprises the following steps:
Implementing the process according to the invention, for the sweet whey material, wherein the resins absorbs a percentage P1 of cGMP present in the sweet whey, obtaining a first protein material, measuring the content of tryptophan (Trp) and threonine (Thr) in the first protein material so that to obtain a ratio Trp/Thr1;
Implementing the process according to the invention, for the sweet whey material, wherein the resins absorbs a percentage P2 of cGMP present in the sweet whey, obtaining a second protein material, measuring the content of tryptophan (Trp) and threonine (Thr) in the second protein material so that to obtain a ratio Trp/Thr2;

Drafting the linear calibration curve in a graph providing the cGMP percentage absorbed by the resin with respect to the Trp/Thr ratio, by positioning the plots (Trp/Thr1; P1) and (Trp/Thr2; P2) in the graph and drawing a line through these two plots;

Determining the specific ratio of cGMP present in the sweet whey that the resins should absorb with respect to the targeted thryptophan/threonine ratio by the use of the linear calibration curve which was drawn up; and Implementing the process according to the invention on the sweet whey material wherein the resins absorbs the specific ratio of cGMP present in the sweet whey, so that so that to obtain the protein material having the targeted tryptophan/threonine ratio.

The method is advantageously such that it is possible to adapt the process according to the invention, for each sweet whey protein material, so as to fit the targeted Tryptophan/Threonine ratio of the protein material. Said Tryptophan/Threonine ratio is generally chosen for the suitability of the protein material in infant formulae preferably in hypoallergenic infant formulae.

Without wishing to be bound by any theory, it is believed that the fact that the process according to the invention is carried out for a sufficient time so that the resin absorbs 30 to 42 g/L of the cGMP allows the drafting of this linear calibration curve.

DETAILED DESCRIPTION

For a complete understanding of the present invention and the advantages thereof, reference is made to the following detailed description of the invention.

It should be appreciated that various embodiments of the present invention can be combined with other embodiments of the invention and are merely illustrative of the specific ways to make and use the invention, and do not limit the scope of the invention when taken into consideration with the claims and the following detailed description.

In the present description, the following words are given a definition that should be taken into account when reading and interpreting the description, examples and claims.

As used herein, the following terms have the following meanings.

The term "suitable for infant formulae" means that the product can be directly used in infant formulae, without any adaptation. This means that there is no need for mixing the product with at least one different source of proteins and/or adding selected amino acids.

The term "removal of a compound" means that the compound present in a product is absorbed in the resin thereby producing a product having a lower content of the compound. The corresponding percentage is the percentage of the compound in the product which is removed from the product by absorption in the resin.

The term "infant" means a child under the age of 12 months.

The term "infant formula" means a foodstuff intended for particular nutritional use by infants during the first four to six months of life and satisfying by itself the nutritional requirements of this category of person (Article 1.2 of the European Commission Directive 91/321/EEC of May 14, 1991 on infant formulae and follow-on formulae). See also the exemption of the EU directive.

As used in this specification, the words "comprises", "comprising", and similar words, are not to be interpreted in an exclusive or exhaustive sense. In other words, they are intended to mean "including, but not limited to".

Any reference to prior art documents in this specification is not to be considered an admission that such prior art is widely known or forms part of the common general knowledge in the field.

In a preferred embodiment of the process according to the invention, the treating is carried out for a sufficient time so that the resin absorbs between 10 and 90% of the cGMP present in the sweet whey.

Advantageously, the resin absorbs at least 90% of the anions present in the sweet whey. Said anions are usually selected from the group consisting of chlorine, phosphorous, citrate, sulphate and lactate. In particular, the resin advantageously absorbs at least 90% of the chlorine and of the phosphorous present in the sweet whey.

In a preferred embodiment of the process according to the invention, the treatment of the sweet whey in the fluidized bed reactor is implemented at a ratio of protein over resin of 0.10 to 0.35, preferably 0.20 to 0.35, kg protein/L of resin.

In a preferred embodiment of the process according to the invention, the treatment of the sweet whey in the fluidized bed reactor is implemented at a ratio of 0.25 to 1.25 kg dry matter per liter of resin.

In a preferred embodiment of the method according to the invention, P1 is 55% and P2 is 90%.

The decationising step does not change substantially the content of anions or cGMP in the sweet whey material. Thus, the absorption in the resin of the cGMP and anions can relate either to their content in the sweet whey material or to their content in the sweet whey material. We choose here to refer to their content in the sweet whey.

The quantity of cGMP over resin allows the process according to the invention and the method according to the invention to be adapted for any fluidized bed reactor, since the cGMP quantity is representative of the sweet whey material and the resin is representative of the reactor design.

The maximum the resin can bound the cGMP helps the user to determine the quantity of sweet whey materiel to be treated, once the volume of resin is known.

The reaction duration can be monitored by HPLC analysis of the liquid present in the fluidized bed reactor, in order to check the cGMP content of said liquid. The reaction duration can also be monitored by the measurement of the pH value of said liquid: once the pH reaches a constant, the reaction is ended. However, HPLC analysis is preferred since the monitoring by HPLC is more accurate.

The cGMP can be initially measured in the sweet whey material or roughly estimated to be 20% of the protein content of the sweet whey material. An initial cGMP measurement by HPLC is preferred according to the invention.

According to the invention, the sweet whey material can be one of sweet whey obtained after separation of casein coagulated with rennet, a concentrate of sweet whey, a sweet whey or such a whey demineralized to by electrodialysis, ion exchange, reverse osmosis, electrodeionisation or a combination of these procedures, a concentrate of sweet whey demineralized by electrodialysis, ion exchange, reverse osmosis, electrodeionisation or a combination of these procedures, a concentrate of proteins of substantially lactose-free sweet whey obtained by ultrafiltration, followed by diafiltration (ultrafiltration with washing), mother liquors of the crystallization of lactose from sweet whey, a permeate of ultrafiltration of a sweet whey, the product of hydrolysis, by a protease, of a native casein obtained by acid precipitation of skimmed milk with an inorganic acid or by biological acidification, obtained by microfiltration of a skimmed milk, or the product of hydrolysis of a caseinate by a protease. Preferably, the sweet whey has a solid content of about 6 to 30 percent by weight after its decationisation.

The sweet whey material is usually a liquid which can be obtained from dispersion and/or dissolution of solid whey powders in a liquid.

Advantageously, the resin is treated with an alkaline material prior to contact with the sweet whey. Preferably, the sweet whey contacts the resin in a gently stirred reactor at a temperature of less than 50° C. for one to ten hours to adsorb the suitable amount of cGMP onto the resin. A suitable resin is one that is basic and in macroporous or macrocross-linked gel form. The sweet whey usually contacts the resin until the treated liquid material attains a constant pH of between about 4.2 to about 5.8 to indicate that the reaction has proceeded to completion. Advantageously, the sweet whey and the resin are present in a volume ratio of 1:1 to 30:1, preferably 1:2 to 1:10.

The protein material obtained by the method according to the invention is a protein source intended for use by humans, in particular infants, in nutritional foods, in particular in infant formulae. The terms "intended for use by" means that they are specifically adapted for the nutritional needs of the targeted human population. The skilled person is aware of the ingredients useful for such nutritional compositions, in addition to the protein material according to the invention, so as to make them suitable as supplements or nutritionally complete compositions.

These nutritional foods fulfil all the dietetic and/or regulatory requirements that is to say that they comprise, in addition to this protein source, additional components such as a source of available carbohydrates and a lipid source.

The chlorine content of the protein material is usually between 1 mg/100 g, preferably between 5 and 80 mg/100 g and/or the phosphorous content of the protein material is between 50 and 150 mg/100 g, preferably between 90 and 160 mg/100 g.

The tryptophan over threonine ratio of the protein material is generally between 0.240 and 0.450, more preferably between 0.300 and 0.430.

The accuracy of the analytical method for measuring the content of the protein material in amino acids is generally +/−8.5% to 11% (by weight). The accuracy of the analytical method for measuring the content of Threonine in the protein material is generally around +/−8.5%. The accuracy of the analytical method for measuring the content of Tryptophan in the protein material is generally around +/−11%.

The protein material is preferably suitable for the production of a hypoallergenic infant formula. A hydrolysis step is generally implemented on this protein material before it is incorporated in said infant formula. Said hydrolysis step is well known to the skilled person. Such a hydrolysis does not change the amino acid profile in particular the Trp/Thr ratio. More generally, several steps can be carried out on the protein material before it is incorporated in the infant formula, as long as it does not change said amino acid profile in particular the Trp/Thr ratio. Advantageously according to the invention, there is no addition of another protein source or amino acids in the protein material obtained by the process according to the invention.

Figure 1:
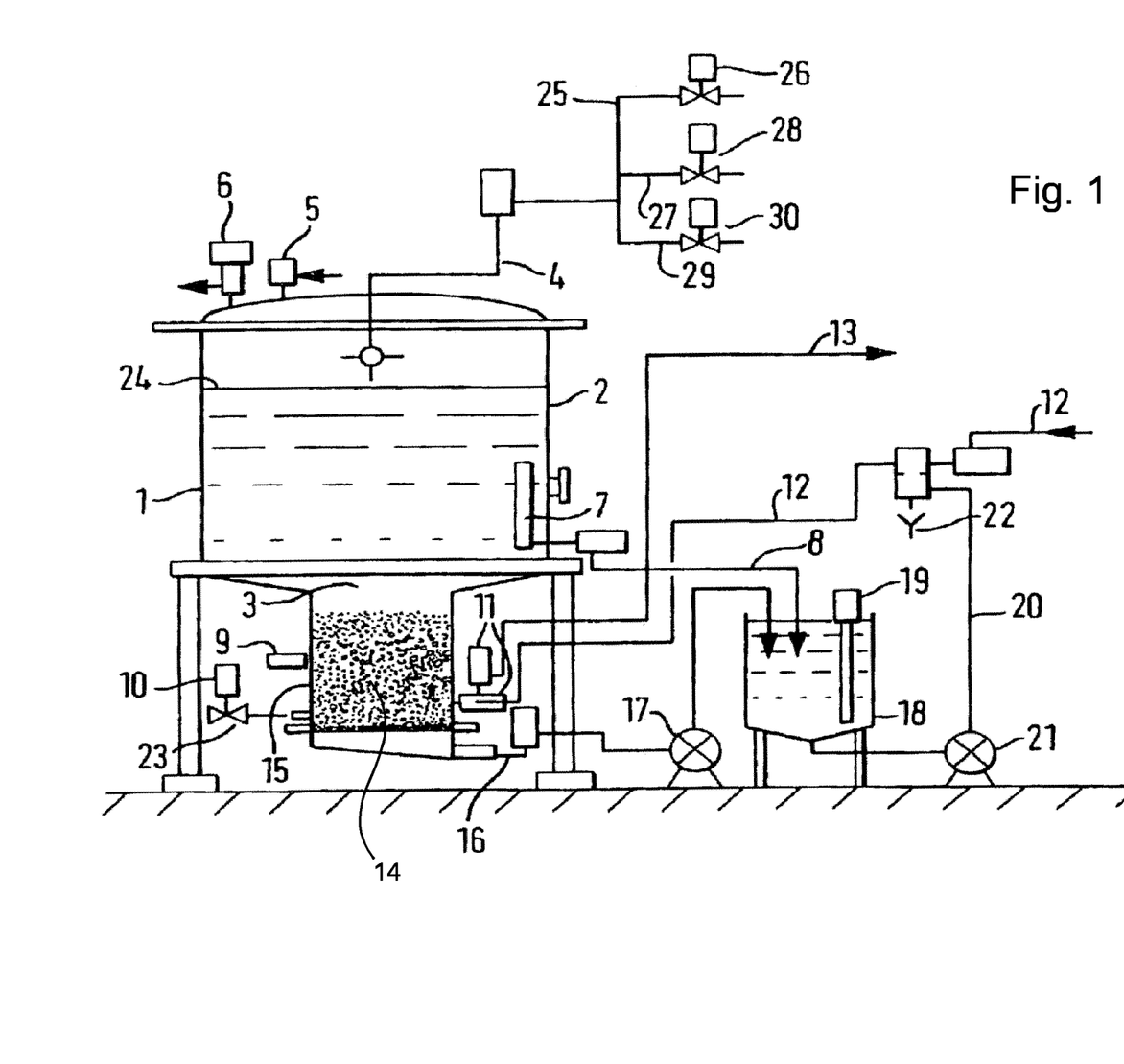
FIG. 1 is a schematic representation of a device for use in a process of the present invention.

FIG. 1 illustrates a device for use in the method of the present invention. A reactor 1 has in its upper section a principal tank 2 connected to a lower part having a compartment 3 through a smaller diameter than that of the tank 2. Tank 2 has a rinsing liquid inlet channel 4, an inlet 5 to allow entry of pressurized gas, a safety valve 6 to regulate the gas pressure in reactor 1. Close to the base of tank 2 there is a strainer 7 and a channel 8 for drawing off liquid.

Connected to compartment 3, the reactor has a pH-meter 9, a gas inlet 10 and a three-way valve 11 connected to an inlet channel 12 for liquid to be treated and a discharge channel 13 to remove treated liquid. The base of compartment 3 has a grid or a perforated plate 14 which collects resin beads 15. Under grid 14, a drawing-off channel 16 removes the liquid via pump 17 to a buffer tank 18, which has a level controlling device 19. Channel 20 via pump 21 removes liquid from buffer tank 18. Channel 20 is connected either to the channel 12, or to the discharge overflow 22.

The process using the device is now described, which was implemented in the following examples.

The initial sweet whey material (dispersion of powder whey in water), was formerly decationised by the means of cationic resin columns in the successive order: weak/strong/strong. The resulting sweet whey was introduced via channel 12 into reactor 1. Air was introduced by bubbling into compartment 3 through the base by the inlet 10 via a non-return valve 23. A fluidized bed of resin beads 15 was created comprising weakly anionic resin of hydrophobic matrix based on polystyrene (IMAC HP 661, Rohm & Haas, regenerated in OH⁻ form). The resin beads 15 were stirred for 4 h in contact with the dispersion due to the turbulence created by the fluidization. The pH of the liquid was constantly controlled by means of the pH-meter 9. Constant analysis of the sweet whey by high-performance liquid chromatography ("HPLC") (not shown) showed when the reaction removed 55% of the cGMP present in the sweet whey. At this point, the desired content of cGMP being removed, the air supply at inlet 10 was cut off and air was introduced through inlet 5 at the top of the reactor above the liquid level 24. The liquid was pressurized and the resin beads settled in the lower part of compartment 3 of reactor 2 where they were retained by grid 14. The treated liquid material was drawn off by gravity and/or pumping through channel 8 and through channel 16 by means of pump 17 towards buffer tank 18. The treated liquid material was then discharged by channel 20 by means of pump 21 and directed towards the outlet by channels 12 and 13.

The treated liquid material was standardized and pH adjusted, concentrated by evaporation or nano filtration and the concentrate was spray-dried in a drying tower.

The recovery of cGMP is optional. It is nevertheless illustrated in FIG. 1. To recover the cGMP, the reactor and the resin were washed with deionised water introduced through inlet channel 25, via valve 26, and inlet channel 4 and flushed through the reactor via channels 12 and 13. The cGMP was eluted twice through the same circuit with aqueous 2% NaOH introduced via channel 27 and valve 28 and rinsed with 30 l of deionised water. After combining the eluate and washing volumes, the volume was concentrated by ultrafiltration or nanofiltration with a membrane having a nominal cut-off of 3000 daltons to obtain a retentate and a filtrate. The retentate was freeze-dried.

Periodically, the resin could be subjected to acidic regeneration after alkaline regeneration once the equivalent of 10 volumes of resin bed had been treated. After elution of the cGMP with the alkaline solution as described above, the resin was washed with a concentrated aqueous solution of HCl supplied by channel 29 and valve 30, followed by water supplied by channel 25 and valve 26. The resin was converted to the OH⁻ form by passing a concentrated aqueous solution of NaOH supplied by channel 27 followed by water from channel 25, into channel 4. The solutions were removed from reactor 1 via channel 16, transferred by pump 17 to the buffer tank 18. From buffer tank 18, the solutions were removed by pump 21, discharged by channel 20 and overflow 22 into the effluent treatment. Following this operation, the resin was ready for another treatment cycle.

The treated liquid was removed and used as a protein material according to the invention.

The invention is further described with reference to the following examples. It will be appreciated that the invention as claimed is not intended to be limited in any way by these examples.

EXAMPLES

Example 1 (According to the Invention): Process Removing Different Percentages of the cGMP from Sweet Whey Material WPC 31.5 and Method for Producing a Protein Material Having a Targeted Trp/Thr Ratio Starting from Sweet Whey Materials Containing cGMP WPC 31.5 and WPC 80

The sweet whey material was whey concentrate WPC 31.5. It was decationised with weak/strong/strong cation exchange resins. The weak resin was IMAC HP 336 and the strong resin was IMAC 1110Na, both sold by Dow Chemical (formerly Rohm & Haas). This sweet whey had a protein content of around 31.5% on DM (for Dry Matter) with a total solid content of 18% and a pH of 1.75. 4420 kg of this sweet whey were pumped into the reactor 1 containing 7500 liters of weak anion exchange resin (HP 661 food grade). The entire sweet whey volume was contacted with the resin. The resin and the sweet whey were suspended together for 4 hours at a temperature of 15 to 18° C. The pH was increasing from 1.75 to a final pH of 5.1 to 5.3 over the 4 hours of reaction time. The cGMP removal was monitored by HPLC.

After 4 hours of reaction time, the resulting demineralized and cGMP depleted whey was pumped out of the reactor. This protein material was pushed out and the resin was washed with water in order to reduce losses on proteins and dry matter. The cGMP was recovered by a combined step of elution and regeneration with 4% NaOH. After the regeneration the NaOH was pushed out with water and rinsed with water until the pH reached around 10.5. Once this pH was reached the reactor was ready for the next production. After standard neutralization with NaOH and KOH, the product was heat treated, evaporated and spray dried.

The data relevant to the process is summarized in Table 1 below.

| | |
|---|---|
| Dry matter (DM) load (kg) | 4420 |
| Resin HP 661 amount (L) | 7500 |
| DM per liter of resin (kg/L) | 0.60 |
| Protein per liter of resin (kg/L) | 0.19 |
| cGMP bound per liter resin (g/L) | 39 |
| NaOH (100%) per kg DM (g/L) | 85 |
| Reaction time (h) | 4 |
| Cycle time (h) | 12 |
| Trp/Thr ratio | 0.42 |

Figure 2:
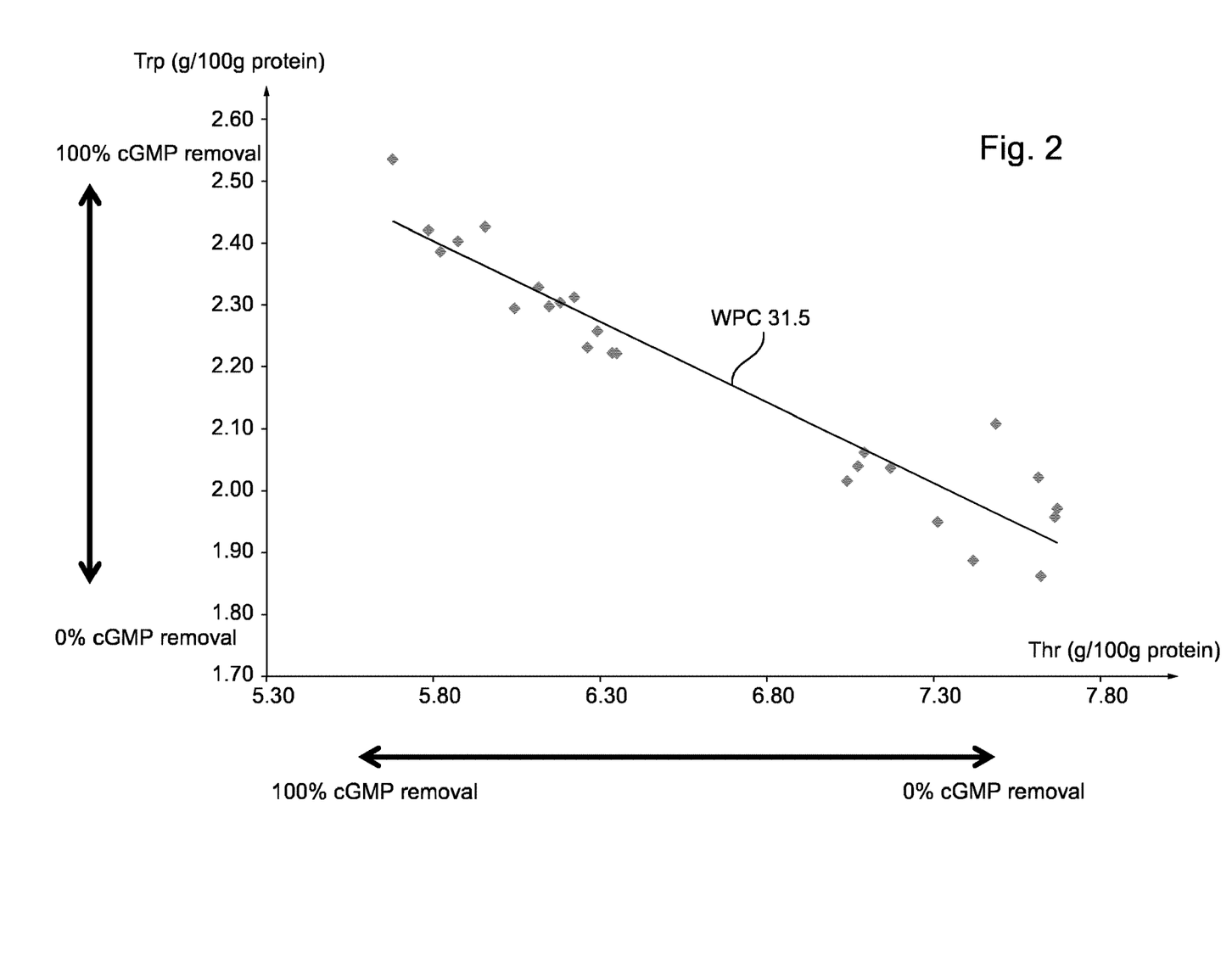
FIG. 2 is a graph providing the Tryptophan (Trp) content with respect to the Threonine (Thr) content, the corresponding percentage of cGMP removal being indicated (see bidirectional arrows), for the sweet whey material WPC 31.5.

The process was repeated several times so that to obtain several plots constituting the graph disclosed in FIG. 2, providing the Tryptophan (Trp) content with respect to the Threonine (Thr) content, for the sweet whey material WPC 31.5. Each plot of the curve data corresponds to measured values of Trp and Thr on a protein material obtained by the treatment process according to the invention, the treatment process being implemented at a given value of cGMP. The corresponding percentage of cGMP removal is roughly indicated in FIG. 2 (see bidirectional arrows). This curve showed a linear relationship between the content of Trp and the content of Thr.

Figure 3:
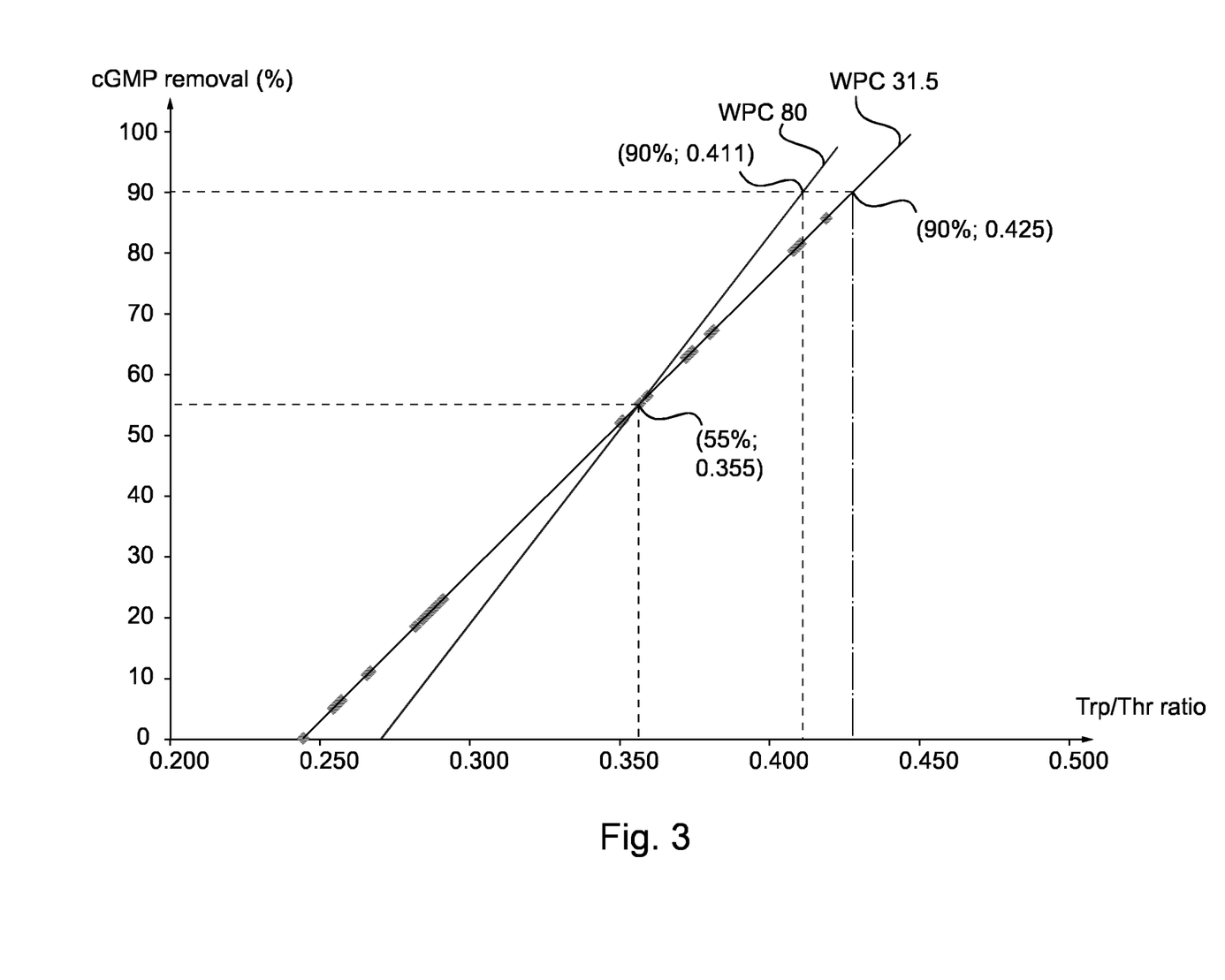
FIG. 3 is a graph showing two calibration curves, one providing the cGMP removal (in percentage) with respect to the Trp/Thr ratio, for the sweet whey material WP 31.5 and the other providing the cGMP removal (in percentage) with respect to the Trp/Thr ratio, for the sweet whey material WP 80.

FIG. 2 led to the calibration curve of FIG. 3 for the sweet whey material WPC 31.5. The calibration curve provides the cGMP removal (in percentage) with respect to the Trp/Thr ratio, for the sweet whey material WP 31.5. This curve shows a linear relationship between the cGMP removal percentage and the Trp/Thr ratio. Similarly, another linear calibration curve was drawn up on the basis of the values found in following examples 4 (plot (0.411; 90%)) and 5 (plot (0.36; 55%)), for the sweet whey material WP 80, by drawing a line through these two plots.

The calibration curves of FIG. 3 are used according to the invention for determining a specific ratio of cGMP to be removed from a given sweet whey material containing cGMP (in this case WPC 31.5 or WPC 80), in order to obtain a protein material having a targeted tryptophan/threonine ratio.

Example 2 (According to the Invention): Process According to the Invention Removing 90% of the cGMP from the Sweet Whey Material This example is based on the same WPC 31.5 at a cGMP removal of 90%, as Example 1. However the reactor was different and the pretreatment of the whey material is different.

The sweet whey material was whey concentrate WPC 31.5. It was electrodialysed, subsequently decationised with weak/strong/strong cation exchange resins and then ultrafiltrated. The weak resin was IMAC HP 336 and the strong resin was IMAC 1110Na, both sold by Dow Chemical (formerly Rohm & Haas). This sweet whey had a protein content of around 31.5% on DM (for Dry Matter) with a total solid content of 18% and a pH of 1.85. 5900 kg of this sweet whey were pumped into the reactor containing 8,500 liters of weak anion exchange resin (HP 661 food grade). The entire sweet whey volume was contacted with the resin. The resin and the sweet whey were suspended together for 4 hours at a temperature of 15 to 18° C. The pH was increasing from 1.85 to a final pH of 5.25 over the 4 hours of reaction time. The cGMP removal was monitored by HPLC.

After 4 hours of reaction time, the resulting demineralized and cGMP sweet whey was reduced by 55% and this protein material was pumped out of the reactor. This protein material was pushed out and the resin was washed with water in order to reduce losses on proteins and dry matter. The cGMP was recovered by a combined step of elution and regeneration with 4% NaOH. After the regeneration the NaOH was pushed out with water and rinsed with water until the pH reached around 10.5. Once this pH was reached the reactor was ready for the next production. After standard neutralization with NaOH and KOH, the product was heat treated, evaporated and spray dried.

The data relevant to the process is summarized in Table 2 below.

| Dry matter (DM) load (kg) | 5900 |
|---|---|
| Resin amount (L) | 8500 |
| DM per liter of resin (kg/L) | 0.69 |
| Protein per liter of resin (kg/L) | 0.22 |
| cGMP bound per liter resin (g/L) | 39 |
| NaOH (100%) per kg DM (g/L) | 63 |
| Reaction time (h) | 4 |
| Cycle time (h) | 12 |
| Trp/Thr ratio | 0.416 |

Taking into consideration the measurement accuracy, the Trp/thr ratio is identical to the result found in Example 1.

Example 3 (According to the Invention): Process According to the Invention Removing 55% of the cGMP from the Sweet Whey Material The sweet whey material was whey concentrate WPC 31.5. It was decationised with weak/strong/strong cation exchange resins. The weak resin was IMAC HP 336 and the strong resin was IMAC 1110Na, both sold by Dow Chemical (formerly Rohm & Haas). This sweet whey had a protein content of around 31.5% on DM (for Dry Matter) with a total solid content of 18% and a pH of 1.75. 6785 kg of this sweet whey were pumped into the reactor containing 8,500 liters of weak anion exchange resin (HP 661 food grade). The entire sweet whey volume was contacted with the resin. The resin and the sweet whey were suspended together for 4 hours at a temperature of 15 to 18° C. The pH was increasing from 1.75 to a final pH of 4.90 over the 4 hours of reaction time. The cGMP removal was monitored by HPLC.

After 4 hours of reaction time, the resulting demineralized and cGMP sweet whey was reduced by 55% and this protein material was pumped out of the reactor. This protein material was pushed out and the resin was washed with water in order to reduce losses on proteins and dry matter. The cGMP was recovered by a combined step of elution and regeneration with 4% NaOH. After the regeneration the NaOH was pushed out with water and rinsed with water until the pH reached around 10.5. Once this pH was reached the reactor was ready for the next production. After standard neutralization with NaOH and KOH, the product was heat treated, evaporated and spray dried.

The data relevant to the process is summarized in Table 3 below.

| Dry matter (DM) load (kg) | 6785 |
|---|---|
| Resin amount (L) | 8500 |
| DM per liter of resin (kg/L) | 0.80 |
| Protein per liter of resin (kg/L) | 0.25 |
| cGMP bound per liter resin (g/L) | 39 |
| NaOH (100%) per kg DM (g/L) | 55 |
| Reaction time (h) | 4 |
| Cycle time (h) | 12 |
| Trp/Thr ratio | 0.36 |

Example 4 (According to the Invention): Process According to the Invention Removing 90% of the cGMP from the Sweet Whey Material The sweet whey material was whey concentrate WPC 80. It was decationised with weak/strong/strong cation exchange resins. The weak resin was IMAC HP 336 and the strong resin was IMAC 1110Na, both sold by Dow Chemical (formerly Rohm & Haas). This sweet whey had a protein content of around 82% on DM (for Dry Matter) with a total solid content of 12% and a pH of 3.40. 3100 kg of this sweet whey were pumped into the reactor containing 11,600 liters of weak anion exchange resin (HP 661 food grade). The entire sweet whey volume was contacted with the resin. The resin and the sweet whey were suspended together for 4 hours at a temperature of 15 to 18° C. The pH was increasing from 3.40 to a final pH of 5.1 to 5.3 over the 4 hours of reaction time. The cGMP removal was monitored by HPLC.

After 4 hours of reaction time, the resulting demineralized and cGMP sweet whey was reduced by 55% and this protein material was pumped out of the reactor. This protein material was pushed out and the resin was washed with water in order to reduce losses on proteins and dry matter. The cGMP was recovered by a combined step of elution and regeneration with 4% NaOH. After the regeneration, the NaOH was pushed out with water and rinsed with water until the pH reached around 10.5. Once this pH was reached the reactor was ready for the next production. After standard neutralization with NaOH and KOH, the product was heat treated, evaporated and spray dried.

The data relevant to the process is summarized in Table 4 below.

| Dry matter (DM) load (kg) | 3100 |
|---|---|
| Resin amount (L) | 11600 |
| DM per liter of resin (kg/L) | 0.27 |
| Protein per liter of resin (kg/L) | 0.22 |
| cGMP bound per liter resin (g/L) | 39 |
| NaOH (100%) per kg DM (g/L) | 168 |
| Reaction time (h) | 4 |
| Cycle time (h) | 12 |
| Trp/Thr ratio | 0.411 |

Thus the protein material obtained by the process according to the invention, with 55% cGMP removal, showed surprisingly the same mineral profile as a 90% removal process which made this protein material suitable as a protein source suitable for hypoallergenic infant formulae.

Example 5 (According to the Invention): Process According to the Invention Removing 55% of the cGMP from the Sweet Whey Material The sweet whey material was whey concentrate WPC 80. It was decationised with weak/strong/strong cation exchange resins. The weak resin was IMAC HP 336 and the strong resin was IMAC 1110Na, both sold by Dow Chemical (formerly Rohm & Haas). This sweet whey had a protein content of around 82% on DM (for Dry Matter) with a total solid content of 12% and a pH of 3.40. 4235 kg of this sweet whey were pumped into the reactor containing 11,600 liters of weak anion exchange resin (HP 661 food grade). The entire sweet whey volume was contacted with the resin. The resin and the sweet whey were suspended together for 4 hours at a temperature of 15 to 18° C. The pH was increasing from 3.40 to a final pH of 4.80 over the 4 hours of reaction time. The cGMP removal was monitored by HPLC.

After 4 hours of reaction time, the resulting demineralized and cGMP sweet whey was reduced by 55% and the sweet whey was pumped out of the reactor. The sweet whey was pushed out and the resin was washed with water in order to reduce losses on proteins and dry matter. The cGMP was recovered by a combined step of elution and regeneration with 4% NaOH. After the regeneration, the NaOH was pushed out with water and rinsed with water until the pH reached around 10.5. Once this pH was reached the reactor was ready for the next production. After standard neutralization with NaOH and KOH, the product was heat treated, evaporated and spray dried.

The data relevant to the process is summarized in Table 5 below.

| | |
|---|---|
| Dry matter (DM) load (kg) | 4235 |
| Resin amount (L) | 11600 |
| DM per liter of resin (kg/L) | 0.37 |
| Protein per liter of resin (kg/L) | 0.30 |
| cGMP bound per liter resin (g/L) | 39 |
| NaOH (100%) per kg DM (g/L) | 123 |
| Reaction time (h) | 4 |
| Cycle time (h) | 12 |
| Trp/Thr ratio | 0.36 |

Thus the protein material obtained by the process according to the invention, with 55% cGMP removal, showed surprisingly the same mineral profile as a 90% removal process which made this protein material suitable as a protein source suitable for hypoallergenic infant formulae.

Although the invention has been described by way of examples, it should be appreciated that variations and modifications may be made without departing from the scope of the invention as defined in the claims. Furthermore, where known equivalents exist to specific features, such equivalents are incorporated as if specifically referred in this specification.

The invention claimed is:

1. A method for producing a protein material from a sweet whey material containing cGMP (caseinoGlycoMacroPeptide), wherein the protein material has a targeted tryptophan/threonine ratio, the method comprising:

implementing a first process comprising decationising a first portion of the sweet whey material to obtain a first sweet whey having a pH value of 1 to 4.5, treating the first sweet whey in a fluidized bed reactor comprising a specific volume of an anionic resin, at a temperature between 10° C. and 18° C., wherein the first sweet whey contacts the resin in the reactor so that the resin absorbs between 10% and 90% of the cGMP present in the first sweet whey, recovering a first protein material, the treating of the first sweet whey is carried out for a sufficient time so that the resin absorbs a percentage P1 of the cGMP present in the first sweet whey, obtaining the first protein material, measuring the content of tryptophan (Trp) and threonine (Thr) in the first protein material to obtain a ratio Trp/Thr1;

implementing a second process comprising decationising a second portion of the sweet whey material to obtain a second sweet whey having a pH value of 1 to 4.5; treating the second sweet whey in a fluidized bed reactor comprising a specific volume of an anionic resin, at a temperature between 10° C. and 18° C., wherein the second sweet whey contacts the resin in the reactor so that the resin absorbs between 10% and 90% of the cGMP present in the second sweet whey, recovering a second protein material, the treating of the second sweet whey is carried out for a sufficient time so that the resin absorbs a percentage P2 of the cGMP present in the second sweet whey, obtaining the second protein material, measuring the content of tryptophan (Trp) and threonine (Thr) in the second protein material to obtain a ratio Trp/Thr2;

drafting a linear calibration curve in a graph providing the cGMP percentage absorbed by the resin with respect to the Trp/Thr ratio, by positioning plots (Trp/Thr1; P1) and (Trp/Thr2; P2) in the graph and drawing a line through these two plots;

determining a specific ratio of cGMP present in the sweet whey that the resin should absorb with respect to the targeted tryptophan/threonine ratio by use of the linear calibration curve which is drawn; and implementing a third process comprising decationising a third portion of the sweet whey material to obtain a third sweet whey having a pH value of 1 to 4.5; treating the third sweet whey in a fluidized bed reactor comprising a specific volume of an anionic resin, at a temperature between 10° C. and 18° C., wherein the third sweet whey contacts the resin in the reactor so that the resin absorbs between 10% and 90% of the cGMP present in the third sweet whey; recovering a third protein material; and wherein the treating of the third sweet whey is carried out for a sufficient time so that the resin absorbs the specific ratio of cGMP present in the third sweet whey to obtain the protein material having the targeted tryptophan/threonine ratio.

2. The method according to claim 1, wherein P1 is 55% and P2 is 90%.

* * * * *